United States Patent
Holmer et al.

(10) Patent No.: US 9,427,513 B2
(45) Date of Patent: Aug. 30, 2016

(54) DETECTING BLOOD PATH DISRUPTION IN EXTRACORPREAL BLOOD PROCESSING

(75) Inventors: Mattias Holmer, Lund (SE); Bo Olde, Lund (SE); Kristian Solem, Kavlinge (SE)

(73) Assignee: Gambro Lundia AB, Lund (SE)

( * ) Notice: Subject to any disclaimer, the term of this patent is extended or adjusted under 35 U.S.C. 154(b) by 513 days.

(21) Appl. No.: 14/129,087

(22) PCT Filed: May 23, 2012

(86) PCT No.: PCT/EP2012/059521
§ 371 (c)(1),
(2), (4) Date: Apr. 11, 2014

(87) PCT Pub. No.: WO2012/175267
PCT Pub. Date: Dec. 27, 2012

(65) Prior Publication Data
US 2014/0298891 A1 Oct. 9, 2014

Related U.S. Application Data

(60) Provisional application No. 61/500,146, filed on Jun. 23, 2011.

(30) Foreign Application Priority Data

Jun. 23, 2011 (SE) ...................................... 1150584

(51) Int. Cl.
*A61M 37/00* (2006.01)
*A61M 1/36* (2006.01)
*G01N 19/00* (2006.01)

(52) U.S. Cl.
CPC ........... *A61M 1/367* (2013.01); *A61M 1/3639* (2013.01); *A61M 1/3653* (2013.01);
(Continued)

(58) Field of Classification Search
CPC ............. A61M 1/367; A61M 1/3639; A61M 1/3653; A61M 1/3655; A61M 1/3656; A61M 1/3661; A61M 1/3669; A61M 2205/13; A61M 2205/3331; A61M 2205/3351; G01N 19/00

USPC .................................................. 604/4.01–6.14
See application file for complete search history.

(56) References Cited

U.S. PATENT DOCUMENTS 6,077,443 A * 6/2000 Goldau .................... A61M 1/16
210/143
6,090,048 A * 7/2000 Hertz ................ A61M 5/16859
600/485

(Continued)

FOREIGN PATENT DOCUMENTS

| CN | 102006898 | 4/2011 |
| CN | 102105182 | 6/2011 |

(Continued)

OTHER PUBLICATIONS

Japanese Office Action dated Mar. 8 2016, corresponding to Japanese Patent Application No. 2014-516246 (4 pages).

*Primary Examiner* — Philip R Wiest
(74) *Attorney, Agent, or Firm* — K&L Gates LLP

(57) ABSTRACT

A device monitors a blood path from a blood vessel access of a human subject through an extracorporeal blood processing apparatus and back to the blood vessel access. A pumping device in the blood path is operable to pump blood through the blood path from the blood withdrawal device to the blood return device. The monitoring device obtains pressure data from a pressure sensor arranged upstream of the pumping device in the blood path, and processes the pressure data for detection of a disruption of the blood path downstream of the pumping device, e.g. caused by VND (Venous Needle Dislodgement). The disruption is detected by evaluating presence/absence of cross-talk pulses at the pressure sensor, where the cross-talk pulses originate from one or more pulse generators in the extracorporeal blood processing apparatus and have propagated on a propagation path in a direction downstream of the pumping device through the blood return device, the blood vessel access and the blood withdrawal device to the pressure sensor.

22 Claims, 5 Drawing Sheets

(52) U.S. Cl.
CPC .......... *A61M 1/3656* (2014.02); *G01N 19/00* (2013.01); *A61M 2205/13* (2013.01); *A61M 2205/3331* (2013.01); *A61M 2205/3351* (2013.01)

(56) References Cited

U.S. PATENT DOCUMENTS

| | | |
|---|---|---|
| 6,663,585 B1 | 12/2003 | Ender |
| 7,341,568 B2 | 3/2008 | Zhang |
| 8,192,388 B2 | 6/2012 | Hogard |
| 8,718,957 B2 | 5/2014 | Furmanski et al. |
| 2005/0010118 A1* | 1/2005 | Toyoda .................. A61B 5/02 600/486 |
| 2005/0065459 A1 | 3/2005 | Zhang et al. |
| 2010/0234786 A1 | 9/2010 | Fulkerson et al. |
| 2011/0034814 A1 | 2/2011 | Kopperschmidt |
| 2011/0040502 A1 | 2/2011 | Furmanski et al. |
| 2011/0106466 A1 | 5/2011 | Furmanski et al. |

FOREIGN PATENT DOCUMENTS

| | | |
|---|---|---|
| DE | 197 34 002 C1 | 9/1998 |
| DE | 199 01 078 C1 | 2/2000 |
| JP | 2005027801 | 2/2005 |
| JP | 2005065888 | 3/2005 |
| JP | 2006-198141 | 8/2006 |
| WO | 97/10013 | 3/1997 |
| WO | 2009/127683 | 10/2009 |
| WO | 2009/156174 | 12/2009 |
| WO | 2009/156175 | 12/2009 |
| WO | 2010/149726 | 12/2010 |

\* cited by examiner

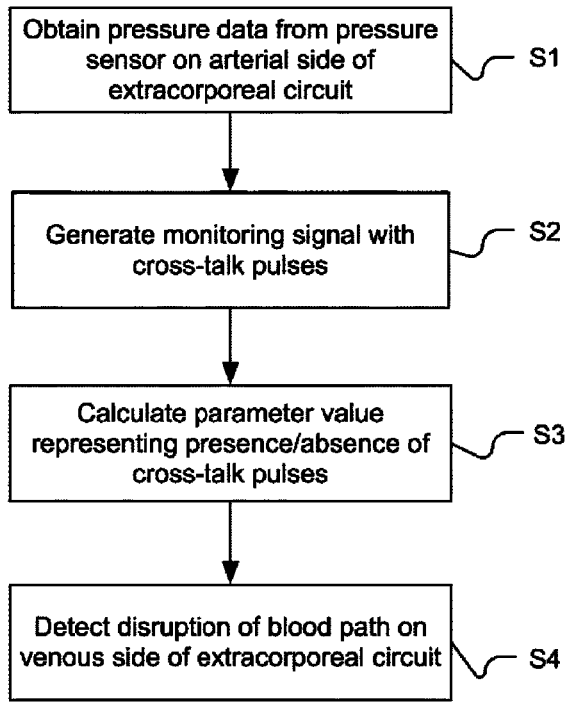
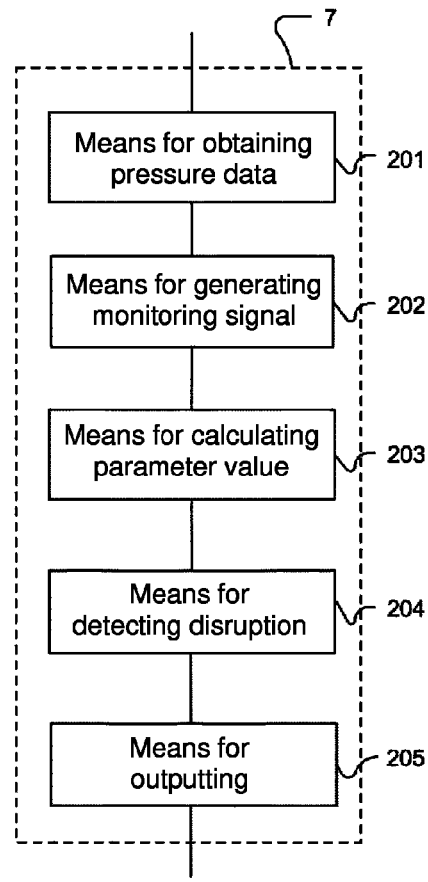
FIG. 2(a)    FIG. 2(b)
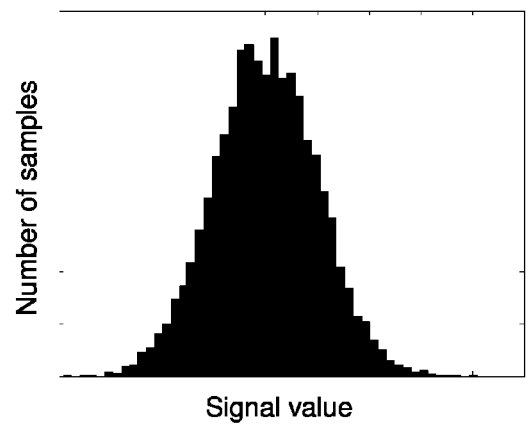
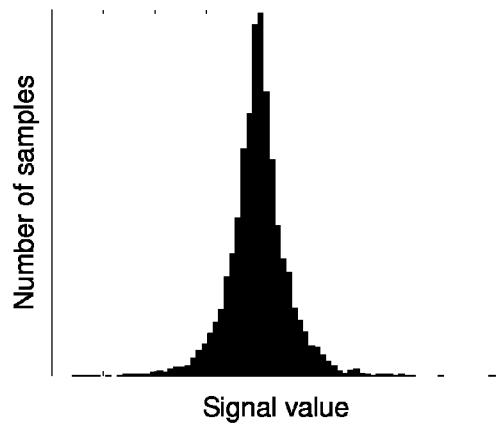
FIG. 4(a)    Fig. 4(b)

DETECTING BLOOD PATH DISRUPTION IN EXTRACORPREAL BLOOD PROCESSING

CROSS RELATED APPLICATION

This application is the U.S. national phase of International Application No. PCT/EP2012/059521 filed 11 Jun. 2012 which designated the U.S. and claims priority to Swedish Patent Application No. 1150584-9 filed 23 Jun. 2011 and U.S. Provisional Patent Application No. 61/500,146 filed 23 Jun. 2011, the entire contents these applications are incorporated by reference.

TECHNICAL FIELD

The present invention relates to a technique for detecting blood path disruption during extracorporeal blood processing, e.g. dialysis, and in particular a disruption downstream of a blood pump in a blood processing apparatus, e.g. caused by a so-called Venous Needle Dislodgement (VND).

BACKGROUND ART

In extracorporeal blood processing, blood is taken out of a human subject, processed (e.g. treated) and then reintroduced into the subject by means of an extracorporeal blood flow circuit ("EC circuit") which is part of a blood processing apparatus. Generally, the blood is circulated through the EC circuit by a blood pump. In certain types of extracorporeal blood processing, the EC circuit includes an access device for blood withdrawal (e.g. an arterial needle) and an access device for blood reintroduction (e.g. a venous needle), which are inserted into a dedicated blood vessel access (e.g. fistula or graft) on the subject. Such extracorporeal blood processing includes hemodialysis, hemodiafiltration, hemofiltration, plasmapheresis, etc.

In extracorporeal blood processing, it is vital to minimize the risk for malfunctions in the EC circuit, since these may lead to a potentially life-threatening condition of the subject. Serious conditions may e.g. arise if the EC circuit is disrupted downstream of the blood pump, e.g. by a VND event, in which the venous needle comes loose from the blood vessel access. Such a disruption may cause the subject to be drained of blood within minutes.

VND may be detected during blood processing based on a pressure signal from a pressure sensor ("venous pressure sensor") on the downstream side of the blood pump in the EC circuit. Conventionally, VND monitoring is carried out by comparing one or more measured pressure levels with one or more threshold values. However, it may be difficult to set appropriate threshold values, since the pressure in the EC circuit may vary between treatments, and also during a treatment, e.g. as a result of the subject moving. Further, if an access device comes loose and gets stuck in bed sheets or the subject's clothes, the measured pressure level might not change enough to indicate the potentially dangerous situation.

WO97/10013 proposes alternative techniques for VND monitoring based on the pressure signal measured by the venous pressure sensor in the EC circuit. In one alternative, VND monitoring is based on detection of heart pulses in the pressure signal. The heart pulses represent pressure pulses produced by a patient's heart and transmitted from the patient's circulatory system to the venous pressure sensor via the blood vessel access and the venous needle. In an alternative, VND monitoring is based on pressure pulses (pump pulses) that are generated by the blood pump and transmitted from the blood pump to the venous pressure sensor via the arterial needle, the blood vessel access and the venous needle. An absence of pump pulses in the pressure signal thereby indicates that the arterial needle and/or the venous needle is dislodged.

US2005/0010118, WO2009/156174 and US2010/0234786 disclose similar or alternative techniques of VND monitoring based on detection of heart pulses in the pressure signal acquired from a venous pressure sensor.

WO2010/149726 discloses techniques for VND monitoring based on detection of physiological pulses other than heart pulses in the pressure signal from the venous pressure sensor. Such physiological pulses originate from the human subject, e.g. from reflexes, voluntary muscle contractions, non-voluntary muscle contractions, the breathing system, the autonomous system for blood pressure regulation or the autonomous system for body temperature regulation.

The prior art also comprises WO2009/127683, which discloses a technique for VND monitoring, by isolating a beating signal in the pressure signal obtained from the venous pressure sensor. The beating signal manifests itself as an amplitude modulation of the pressure signal and is formed by interference between pressure waves generated by a patient's heart and pressure waves generated by the blood pump. An absence of the beating signal indicates that the venous needle is dislodged.

In certain configurations or operating conditions of the EC circuit, the pressure waves generated by the subject's heart or another physiological phenomenon in the human subject may be too weak to be reliably detected in the pressure signal of the venous pressure sensor. Thus, many of the above techniques may be unreliable in these configurations/operating conditions.

Furthermore, there are blood treatment apparatuses that have no venous pressure sensor, or where the venous pressure sensor has a design or placement that does not allow reliable detection of physiological pulses/pump pulses.

There is thus a need for an alternative or supplementary technique for VND monitoring in EC circuits.

SUMMARY

It is an object of the invention to at least partly overcome one or more of the above-identified limitations of the prior art.

One objective is to provide a new technique for detecting a disruption of a blood path downstream of a pumping device in an extracorporeal blood processing apparatus.

Another objective is to provide a disruption detection technique that does not rely on the provision of a venous pressure sensor in the extracorporeal blood processing apparatus, or a disruption detection technique that does not require data from such a venous pressure sensor, even if a venous pressure sensor is present in the extracorporeal blood processing apparatus.

One or more of these objects, as well as further objects that may appear from the description below, are at least partly achieved by means of a monitoring device, a device for monitoring, an apparatus for extracorporeal blood processing, a method of monitoring and a computer-readable medium according to the independent claims, embodiments thereof being defined by the dependent claims.

A first aspect of the invention is a device for monitoring a blood path extending from a blood vessel access of a human subject through an extracorporeal blood processing apparatus and back to the blood vessel access. The blood path comprises a blood withdrawal device and a blood return device for connection to the blood vessel access, and a pumping device operable to pump blood through the blood path from the blood withdrawal device to the blood return device. The device comprises: an input for obtaining pressure data from a pressure sensor arranged upstream of the pumping device in the blood path to detect pressure pulses in the blood pumped through the blood path; and a signal processor connected to said input. The signal processor is configured to: generate, based on the pressure data, a time-dependent monitoring signal comprising cross-talk pulses that originate from one or more pulse generators in the extracorporeal blood processing apparatus and have propagated in a direction downstream of the pumping device through the blood return device, the blood vessel access and the blood withdrawal device to the pressure sensor, process the monitoring signal for calculation of a parameter value that indicates a presence or absence of the cross-talk pulses, and detect, based at least partly on the parameter value, a disruption of the blood path downstream of the pumping device.

The inventive monitoring device enables detection of a disruption of the blood path downstream of the pumping device, i.e. on the venous side of the blood path, based on pressure data from a pressure sensor upstream of the pumping device, i.e. on the arterial side of the blood path. This surprising technical ability opens up for VND detection in an extracorporeal blood processing apparatus that lacks a (suitable) pressure sensor on the venous side. It also opens up for VND detection when existing techniques fail, e.g. if the physiological pulses are absent or too weak to be detected, since the inventive technique does not require physiological pulses to be detected directly or indirectly (e.g. via a beating signal). Furthermore, the inventive technique may be combined with conventional VND techniques to improve reliability of detection. Still further, since physiological pulses may be stronger on the arterial side than on the venous side of the blood path, the inventive technique may be implemented for joint detection of cross-talk pulses and physiological pulses, where absence of cross-talk pulses may indicate venous side (downstream) disruption and absence of physiological pulses may indicate arterial side (upstream) disruption. As used herein, "upstream" and "downstream" refers to positions further up and down, respectively, from the pumping device in relation to the flow of blood in the blood path.

In one embodiment, the signal processor is configured to calculate the parameter value as a measure of irregularity of signal values within a time window of the monitoring signal. The measure of irregularity may include a measure of entropy of the signal values and/or a statistical measure of the signal values. In one embodiment, the statistical measure includes a standardized moment of third order or higher. For example, the statistical measure may include at least one of skewness and kurtosis.

In one embodiment, the signal processor is configured to generate the monitoring signal to comprise physiological pulses that originate from one or more physiological pulse generators in the human subject, wherein the time window is selected so as to include at least part of one physiological pulse.

In one embodiment, the parameter value is calculated to represent a disturbance caused by the superposition of the cross-talk pulses on the physiological pulses.

In one embodiment, the signal processor is configured to generate the monitoring signal by filtering the pressure data to at least suppress interference pulses that originate from the pumping device and have propagated in the blood path in a direction upstream of the pumping device, wherein the filtering is configured to suppress the interference pulses such that the ratio in magnitude between the interference pulses and the physiological pulses in the monitoring signal is less than about $1/10$, preferably less than about $1/50$, and most preferably less than about $1/100$.

In one embodiment, the signal processor is configured to generate the monitoring signal by filtering the pressure data with respect to interference pulses that originate from the pumping device and have propagated in the blood path in a direction upstream of the pumping device, wherein the filtering is configured to suppress the interference pulses compared to the cross-talk pulses, preferably such that the interference pulses are of the same magnitude as the cross-talk pulses or less. For example, the signal processor may be configured to essentially remove the interference pulses when filtering the pressure data to generate the monitoring signal.

In one embodiment, the signal processor is configured to generate the parameter value as a measure of magnitude of the signal values within a time window of the monitoring signal.

In one embodiment, the signal processor is configured to detect the disruption by comparing the parameter value to a reference, which is obtained as an estimate of the parameter value in absence of the cross-talk pulses. In one implementation, the signal processor is configured to obtain the reference based on at least one of a first, second and third basis value, wherein the first basis value is given by the parameter value calculated during a time period in which said at least one pulse generator is disabled, the second basis value is given by the parameter value calculated during a start-up procedure, in which the extracorporeal blood processing apparatus is connected to the blood vessel access via the blood withdrawal device but is disconnected from the blood vessel access downstream of the pumping device, and the pumping device is operated to pump blood from the blood withdrawal device into the extracorporeal blood processing apparatus, and the third basis value is given by the parameter value calculated during a priming procedure, in which the extracorporeal blood processing apparatus is disconnected from the blood vessel access upstream and downstream of the pumping device, and the pumping device is operated to pump a priming fluid to flow into the extracorporeal blood processing apparatus at an upstream end and out of the extracorporeal blood processing apparatus at a downstream end. In such an implementation, the first basis value may be generated to represent presence of physiological pulses that originate from the human subject and absence of said cross-talk pulses and absence of interference pulses that originate from the pumping device and have propagated in the blood path in a direction upstream of the pumping device; the second basis value may be generated to represent one of: presence of said physiological pulses and said interference pulses and absence of said cross-talk pulses; presence of said physiological pulses and absence of said cross-talk pulses and said interference pulses; and presence of said interference pulses and absence of said cross-talk pulses and said physiological pulses; and the third basis value may be generated to represent presence of said interference pulses and absence of said cross-talk pulses and said physiological pulses.

In one embodiment, the signal processor is configured to extract shape-indicative data from the monitoring signal and calculate the parameter value by matching the shape-indicative data to reference profile data. For example, the shape-indicative data may comprise signal values in the monitoring signal, and the reference profile data may comprise a temporal reference profile.

In another embodiment, the signal processor is configured to extract timing data for pulses in the monitoring signal and calculate the parameter value by matching the timing data to a reference timing indicative of a pulse generation process in said one or more pulse generators.

In one embodiment, said one or more pulse generators are included in a dialysis fluid circuit in hydraulic contact with the blood path, and wherein the signal processor is configured to obtain a reference signal from a further pressure sensor arranged in the dialysis fluid circuit to detect pressure pulses in a dialysis fluid pumped through the dialysis fluid circuit or from a control signal for said one or more pulse generators, and calculate the parameter value by matching the monitoring signal to the reference signal.

A second aspect of the invention is a device for monitoring the above-mentioned blood path. The device comprises: means for obtaining pressure data from a pressure sensor arranged upstream of the pumping device in the blood path to detect pressure pulses in the blood pumped through the blood path; means for generating, based on the pressure data, a time-dependent monitoring signal comprising cross-talk pulses that originate from one or more pulse generators in the extracorporeal blood processing apparatus and have propagated in a direction downstream of the pumping device through the blood return device, the blood vessel access and the blood withdrawal device to the pressure sensor; means for processing the monitoring signal for calculation of a parameter value that indicates a presence or absence of the cross-talk pulses; and means for detecting, based at least partly on the parameter value, a disruption of the blood path downstream of the pumping device.

A third aspect of the invention is an apparatus for extracorporeal blood processing, which is configured for connection to the cardiovascular system of a human subject so as to define a blood path extending from a blood vessel access of the human subject and comprising a blood withdrawal device for connection to the blood vessel access, a pumping device operable to pump blood through the blood path, a blood processing unit, and a blood return device for connection to the blood vessel access. In addition, the apparatus comprises the monitoring device of the first aspect.

A fourth aspect of the invention is a method of monitoring the above-mentioned blood path. The method comprises: obtaining pressure data from a pressure sensor arranged upstream of the pumping device in the blood path to detect pressure pulses in the blood pumped through the blood path; generating, based on the pressure data, a time-dependent monitoring signal comprising cross-talk pulses that originate from one or more pulse generators in the extracorporeal blood processing apparatus and have propagated in a direction downstream of the pumping device through the blood return device, the blood vessel access and the blood withdrawal device to the pressure sensor; processing the monitoring signal for calculation of a parameter value that indicates a presence or absence of the cross-talk pulses; and detecting, based at least partly on the parameter value, a disruption of the blood path downstream of the pumping device.

In one embodiment, the parameter value is calculated as a measure of irregularity of signal values within a time window of the monitoring signal. For example, the measure of irregularity may include a measure of entropy of the signal values and/or a statistical measure of the signal values. In one embodiment, the statistical measure includes a standardized moment of third order or higher. For example, the statistical measure may include at least one of skewness and kurtosis.

In one embodiment, the monitoring signal is generated to comprise physiological pulses that originate from the human subject, wherein the time window is selected so as to include at least part of one physiological pulse.

In one embodiment, the parameter value is calculated to represent a disturbance caused by the superposition of the cross-talk pulses on the physiological pulses.

In one embodiment, said processing comprises: filtering the pressure data to at least suppress interference pulses that originate from the pumping device and have propagated in the blood path in a direction upstream of the pumping device, whereby the interference pulses are suppressed such that the ratio in magnitude between the interference pulses and the physiological pulses in the monitoring signal is less than about $1/10$, preferably less than about $1/50$, and most preferably less than about $1/100$.

In one embodiment, said processing comprises: filtering the pressure data with respect to interference pulses that originate from the pumping device and have propagated in the blood path in a direction upstream of the pumping device, whereby the interference pulses are suppressed compared to the cross-talk pulses, preferably such that the interference pulses are of the same magnitude as the cross-talk pulses or less. For example, said processing may comprise essentially removing the interference pulses when filtering the pressure data to generate the monitoring signal.

In one embodiment, said processing comprises: generating the parameter value as a measure of magnitude of the signal values within a time window of the monitoring signal.

In one embodiment, said detecting comprises: comparing the parameter value to a reference, which is obtained as an estimate of the parameter value in absence of the cross-talk pulses.

In one embodiment, said processing comprises: extracting shape-indicative data from the monitoring signal, and calculating the parameter value by matching the shape-indicative data to reference profile data.

In another embodiment, said processing comprises: extracting timing data for pulses in the monitoring signal, and calculating the parameter value by matching the timing data to a reference timing indicative of a pulse generation process in said one or more pulse generators.

In one embodiment, said one or more pulse generators are included in a dialysis fluid circuit in hydraulic contact with the blood path, and the method further comprises: obtaining a reference signal from a further pressure sensor which is arranged in the dialysis fluid circuit to detect pressure pulses in a dialysis fluid pumped through the dialysis fluid circuit or from a control signal for said one or more pulse generators; and calculating the parameter value by matching the monitoring signal to the reference signal.

A fifth aspect of the invention is a computer-readable medium comprising computer instructions which, when executed by a processor, cause the processor to perform the method of the fourth aspect.

The second to fifth aspects share technical effects with the first aspect, and any one of the embodiments of the first aspect may be combined with the second to fifth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

FIG. 2(a) is a flow chart of an embodiment of a method for VND detection, and FIG. 2(b) is a block diagram of an embodiment of a device for VND detection.

FIGS. 4(a)-4(d) are histograms of data samples representing a normal distribution, a Laplace distribution, a uniform (stochastic) distribution and a sinusoidal distribution, respectively.

DETAILED DESCRIPTION OF EXAMPLE EMBODIMENTS

Figure 1:
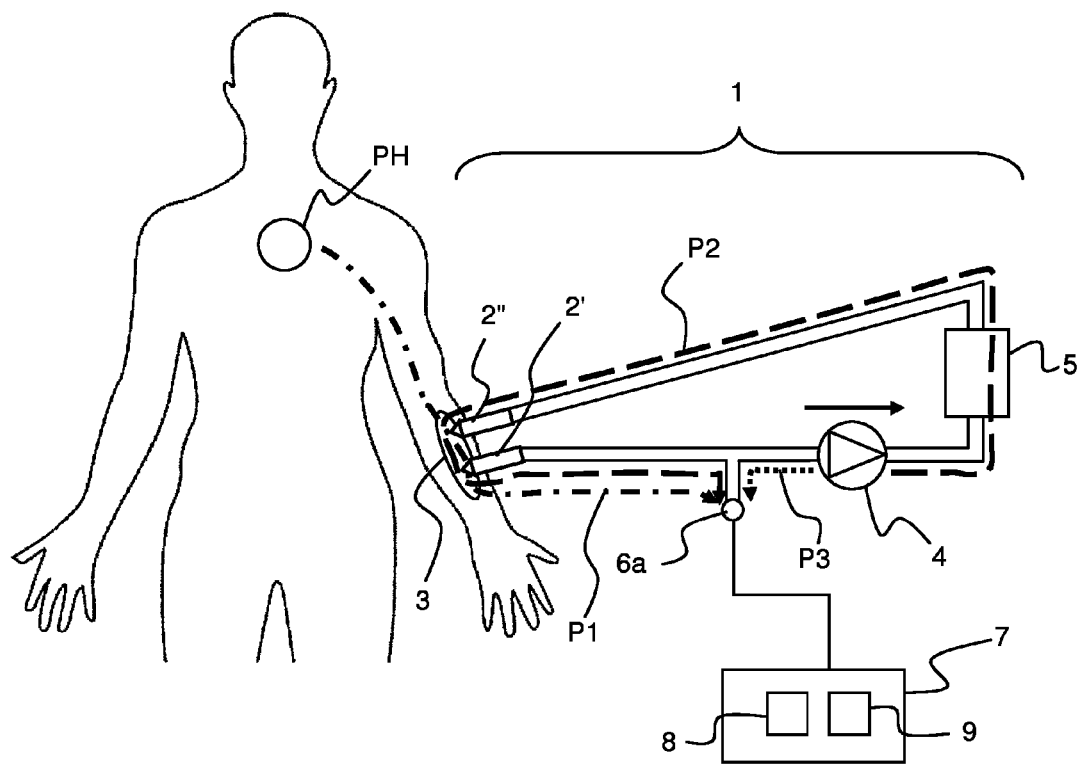
FIG. 1 a schematic diagram of a blood path in an extracorporeal blood processing apparatus attached to a human subject.

Throughout the description, the same reference numerals are used to identify corresponding elements.

FIG. 1 illustrates a human subject which is connected to an extracorporeal fluid circuit 1 by way of access devices 2', 2" inserted into a dedicated vascular access 3 (also known as "blood vessel access") on the subject. The extracorporeal fluid circuit 1 (denoted "EC circuit" in the following) is configured to communicate blood to and from the cardiovascular system of the subject. In one example, the EC circuit 1 is part of an apparatus for blood processing, such as a dialysis machine (cf. 80 in FIG. 8). In the illustrated example, a blood pump 4 draws blood from the vascular access 3 via access device 2' and pumps the blood through a blood processing unit 5, e.g. a dialyzer, and back to the vascular access 3 via access device 2". Thus, when both access devices 2', 2" are connected to the vascular access 3, the EC circuit 1 defines a blood path that starts and ends at the vascular access 3. The EC circuit 1 may be seen to comprise a "venous side" which is the part of the blood path located downstream of the blood pump 4, and an "arterial side" which is the part of the blood path located upstream of the blood pump 4.

A pressure sensor 6a (denoted "arterial pressure sensor" or "arterial sensor") is arranged to detect pressure waves on the arterial side of the EC circuit 1. As used herein, a "pressure wave" is a mechanical wave in the form of a disturbance that travels or propagates through a material or substance. In the context of the following examples, the pressure waves propagate in the blood in the cardiovascular system of the subject and in the blood path of the EC circuit 1 at a velocity that typically lies in the range of about 3-20 m/s. The arterial sensor 6a, which is in direct or indirect hydraulic contact with the blood, generates pressure data that forms a pressure pulse for each pressure wave. A "pressure pulse" is thus a set of data samples that define a local increase or decrease (depending on implementation) in signal magnitude within a time-dependent measurement signal ("pressure signal"). The arterial sensor 6a receives pressure waves on different propagation paths P1, P2, P3 as indicated in FIG. 1.

On propagation path P1, pressure waves generated by a physiological source PH in the human subject propagate through the cardiovascular system of the subject to the vascular access 3 and via the arterial access device 2' to the arterial sensor 6a, which measures corresponding physiological pulses. The pressure waves also enter the venous side of the EC circuit 1 via the venous access device 2", but the pressure waves are typically weak and will be essentially absorbed by the dialyzer 5 and the blood pump 4 and are generally not detected by the arterial sensor 6a. The physiological source PH may be any physiological phenomenon such as the heart, the breathing system, the autonomous system for blood pressure regulation, the autonomous system for body temperature regulation, reflex actions, voluntary muscle contractions and non-voluntary muscle contractions. It is also conceivable the physiological source PH is a mechanical device which is attached to the subject and which shakes, vibrates or pressures on the skin of the patient so as to generate the pressure waves. In another alternative, such a mechanical device may be attached to a support for the subject, e.g. a bed. In the following examples, however, it is assumed that the physiological pulses originate from the subject's heart and are denoted "heart pulses". However, all examples are equally applicable to physiological pulses originating from, alone or in combination, any of the other physiological phenomena listed above as well as the above-mentioned mechanical device.

On propagation path P2, pressure waves generated by the blood pump 4 travel on the venous side of the EC circuit 1 to the venous access device 2", where they enter the vascular access 3. Here, part of the pressure waves enter the arterial side of the EC circuit 1 via the arterial access device 2' and reach the arterial sensor 6a. Since these pressure waves propagate from the venous side to the arterial side of the EC circuit 1, the corresponding pressure pulses are denoted "cross-talk pulses" herein. Thus, unless otherwise stated, the following description assumes that the cross-talk pulses originate from one or more blood pumps in the EC circuit.

It should be noted that the cross-talk pulses may originate from other mechanical pulse generators in the EC circuit 1 or in the apparatus for blood processing. For example, vibrations may be generated by a one or more existing components in the dialysis fluid circuit (cf. 15 in FIG. 8, below), such as a valve, a balancing chamber, a pump for dialysis fluid, etc. These vibrations may be transferred into the blood path via the dialyzer 5 and form cross-talk pulses at the arterial sensor 6a. Irrespective of origin, vibrations may enter the blood path via the tubing on the venous side of the EC circuit 1. Vibrations may alternatively be generated by a dedicated vibrator which is attached to the apparatus for blood processing in an appropriate location for generating the cross-talk pulses.

On propagation path P3, pressure waves generated by the blood pump 4 travel on the arterial side of the EC circuit 1 to the arterial sensor 6a, which generates pressure pulses denoted "upstream pulses" herein (or generally "interference pulses"). The upstream pulses may also originate from other mechanical pulse generators in the EC circuit 1 or in the apparatus for blood processing, e.g. by vibrations that enter the EC circuit 1 on its venous or arterial side and propagate in a direction upstream to the arterial sensor 6a, or by swinging movements occurring in suspended blood lines that define the blood path on the arterial side.

A surveillance device 7 is connected to the arterial sensor 6a by way of a transmission line to acquire and process an electrical signal (denoted "pressure signal" in the following) which is representative of the detected pressure waves. Specifically, the surveillance device 7 is configured to process the pressure signal for detection of a disruption of the blood path on the venous side of the blood pump 4, e.g. caused by a dislodgement of the venous access device 2" from the vascular access 3. In the example of FIG. 1, the surveillance device 7 comprises a signal processor 8 and electronic memory 9.

The surveillance device implements a method which is illustrated in the flow chart of FIG. 2(a). The method is based on the insight that it is possible to detect cross-talk pulses at the arterial sensor 6a, and that a disruption on the venous side will prevent pressure waves from propagating from the venous side to the arterial side via the vascular access 3. Thus, an absence of cross-talk pulses in the pressure signal is used as an indicator of a disruption.

In step S1, the pressure signal is acquired from the arterial sensor 6a. In step S2, a time-dependent monitoring signal is generated based on the pressure signal such that the monitoring signal contains cross-talk pulses, if the EC circuit 1 is intact and properly connected to the vascular access 3. It is to be noted that the cross-talk pulses in the monitoring signal need only be a subset of the cross-talk pulses in the pressure signal. For example, the monitoring signal may be generated to contain signal components of the cross-talk pulses in one or more confined frequency ranges. Depending on implementation, the monitoring signal may be generated to also contain additional pulses, as will be described further below. In step S3, the monitoring signal is processed for calculation of a parameter value that indicates a presence or absence of the cross-talk pulses. Finally, in step S4, the parameter value is evaluated for detection of a downstream disruption of the blood path, e.g. by comparing the parameter value to a reference such as a threshold value or a range.

It is to be understood that the surveillance device 7 executes the method in FIG. 2(a) at selected time steps during operation of the blood processing apparatus, so as to continuously or intermittently assess the status of the venous side of the blood path. In one example, step S1 operates to acquire pressure data at a given sampling rate and step S2 concurrently generates the monitoring signal based on the pressure data, whereas step S3 is executed intermittently or continuously to calculate the parameter value based on the signal values within a time window in the monitoring signal. In another example, steps S1-S3 are executed at selected times to acquire pressure data in a given time window, generate the monitoring signal and calculate the parameter value. In either example, each time window may be defined to contain at least part of a cross-talk pulse, and consecutive time windows may be overlapping or non-overlapping. It is also conceivable that the time window is defined to include more than one cross-talk pulse.

As noted above, step S2 may be implemented to generate the monitoring signal with different content of pulses.

In a first variant, the monitoring signal is generated to only contain the cross-talk pulses. Thus, to the extent that the pressure signal contains heart pulses and upstream pulses, these pulses are removed when generating the monitoring signal, e.g. by appropriate filtering. The filtering may be performed in the time domain, the frequency domain, or both. For example, heart pulses (and other physiological pulses) and upstream pulses may be at least partly removed by operating low-pass filters, high-pass filters, notch filters, or the like on the pressure signal. Upstream pulses may e.g. be removed by the use of temporal profiles of the upstream pulses, which may be input to an adaptive filter structure or directly subtracted from the pressure signal, e.g. as disclosed in WO2009/156175 which is incorporated herein in its entirety by reference. Further filtration techniques that may be used for removal of heart pulses and/or upstream pulses in the pressure signal are disclosed in aforesaid WO97/10013, US2005/0010118, WO2009/156174 and US2010/0234786. In another example, the heart pulses may be inherently absent in the pressure signal, if the pressure waves from the heart are too weak to be detected by the arterial sensor 6a.

It should be noted that the upstream pulses and the cross-talk pulses may have different shapes, and thereby different frequency content (i.e. different distribution of energy over the included frequencies), even if they both originate from the same source, e.g. the blood pump 4. For example, it is well-known that the blood pump-generated pressure pulsations differ between the venous side and the arterial side. It is also possible that the pressure waves from the pump 4 are further modified when they pass the vascular access 3. Thus, cross-talk pulses may be distinguished from upstream pulses.

In a second variant, the monitoring signal is generated to contain cross-talk pulses and heart pulses, but no upstream pulses. The upstream pulses may be removed by filtering, e.g. as described in relation to the first variant. One advantage of the second variant is a reduced need for filtering, since heart pulses may be retained. Another advantage is that the second variant makes it possible to distinguish between a disruption on the venous side and a disruption on the arterial side, since the former will result in absence of cross-talk pulses, and the latter will result in absence of both heart pulses and cross-talk pulses.

Figure 3:
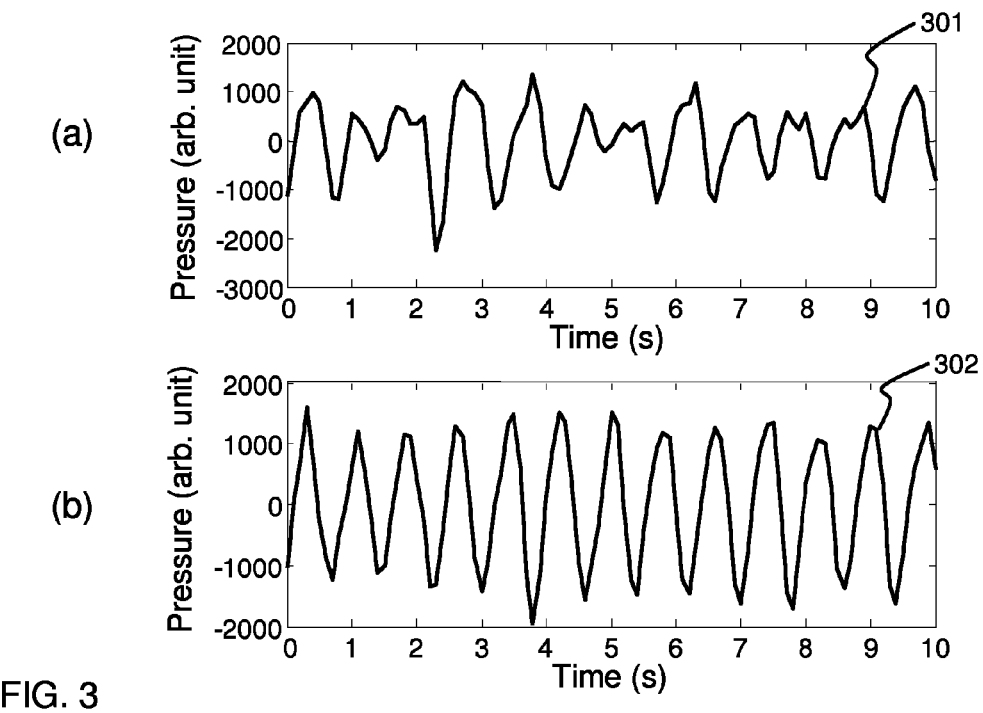
FIGS. 3(a)-3(b) are plots of a monitoring signal before and after a VND event, respectively.

FIG. 3(a) illustrates a monitoring signal 301 obtained with an intact connection between the EC circuit 1 and the vascular access 3. The monitoring signal 301 therefore contains cross-talk pulses superimposed on heart pulses. FIG. 3(b) illustrates a monitoring signal 302 when the venous access device 2" is dislodged from the vascular access 3, which is indicated by a disappearance of the cross-talk pulses, leaving only heart pulses (and signal artifacts such as noise).

In a third variant, the monitoring signal is generated to contain cross-talk pulses, heart pulses and upstream pulses. This may further reduce, or even eliminate, the need for filtering. However, the upstream pulses are typically much stronger than the cross-talk pulses, and to facilitate detection of the cross-talk pulses it may be desirable to suppress the magnitude of the upstream pulses, e.g. by filtering as described in relation to the first variant. In one example, upstream pulses are sufficiently suppressed when the ratio in magnitude between the upstream pulses and the heart pulses is less than about $\frac{1}{10}$, $\frac{1}{50}$, or $\frac{1}{100}$. In another example, the upstream pulses are suppressed compared to the cross-talk pulses, such that the upstream pulses are of the same magnitude as the cross-talk pulses or less.

In a fourth variant, the monitoring signal comprises cross-talk pulses and upstream pulses, but no heart pulses. Like in first variant, the heart pulses may be removed by filtering, or they may be inherently absent in the pressure signal. Like in the third variant, the upstream pulses may be filtered for suppression in relation to the cross-talk pulses.

Returning to the method in FIG. 2(a), the parameter values may be calculated (step S3) in different ways, and the implementation of step S3 may differ depending on the pulse content of the monitoring signal.

In one embodiment, the parameter value is calculated as a magnitude measure of the signal values in the time window of the monitoring signal.

The magnitude measure may be obtained by processing the signal values of the monitoring signal in the time domain and may be given by, e.g., a peak value, a sum of signal values or a sum of squared signal values, possibly with respect to a base line, an energy measure, or an average of signal values, where the signal values are given within a time window or a pulse detected within the time window. Alternatively, the signal values may be processed in the frequency domain, e.g. by Fourier analysis of the monitoring signal/time window. The magnitude measure may be given by, e.g., the spectral density value of a peak in a resulting Fourier spectrum.

A disruption on the venous side may be detected (step S4) as a decrease in the magnitude measure. The magnitude measure is useful with all variants of the monitoring signal.

In another embodiment, the parameter value is calculated as a matching measure. The matching measure may be calculated by comparing the signal values or a curve fitted to the signal values to a reference profile or waveform, and may represent the similarity or difference therebetween. The signal values/fitted curve thus forms "shape-indicating data". For example, the matching measure may be given by a correlation value, a sum of differences between the shape-indicating data and the reference profile, or any suitable l2-norm evaluated based on these differences, such as an $L^1$-norm (sum of absolute differences, aka Manhattan norm) or an $L^2$-norm (Euclidian norm). In calculating the matching value, the signal values/fitted curve and/or the reference profile may be weighted by a suitable function, e.g. to reduce the impact of certain parts within the time window.

The reference profile may represent a disrupted state (no cross-talk pulses) or an intact state (cross-talk pulses) of the EC circuit 1. It is also conceivable to match the signal values to more than one reference profile, e.g. one reference profile representing the disrupted state and one reference profile representing the intact state, which results in more than one matching measure to be evaluated in step S4 (FIG. 2(*a*)). In a further variant, the shape-indicating data may be obtained in the frequency domain, e.g. as an amplitude and/or phase spectrum, which is matched to a corresponding reference amplitude/phase spectrum.

The matching measure is useful with all variants of the monitoring signal. In the first variant, the reference profile may be defined to represent the cross-talk pulses, if these have a known and reproducible shape. It may also be useful with second, third and fourth variants, e.g. if the reference profile is defined to represent the monitoring signal (i.e. the shape of the heart pulses and/or upstream pulses) in the disrupted state.

In another variant of matching, which is useful whenever the monitoring signal is dominated by the cross-talk pulses, the reference signal is generated to represent the operation of the origin of the cross-talk pulses, be it a blood pump 4 in the EC circuit 1 or any other mechanical pulse generator. In one example, the reference signal is given by, or is obtained by extracting data from, an origin control signal which contains pulses that represent the pulse generation process of the origin (which is a pulse generator). In another example, the origin control signal is associated with a default pressure waveform (temporal pressure profile), and the reference signal is generated by modifying the default signal waveform (e.g. rate and/or amplitude of pulses) based on the origin control signal. In yet another example, the reference signal is given by, or is obtained by processing, a pressure signal from another pressure sensor in the apparatus for blood processing. It is realized that the matching may be implemented to match pulse shapes and/or pulse timing between the monitoring signal and the reference signal.

In a specific example, the cross-talk pulses originate from a pulse generator in the dialysis fluid circuit (cf. 15 in FIG. 8, below) and the matching measure is generated by matching the monitoring signal to a reference signal obtained from a pressure sensor (cf. 6*d* in FIG. 8, below) in the dialysis fluid circuit. Such a pressure sensor is normally present the dialysis fluid circuit. The pressure signal from the pressure sensor may be used as the reference signal, optionally after filtering for isolation of pulses from the pulse generator. Optionally, the reference signal may be generated by inputting the (filtered) pressure signal to an algorithm that estimates the response of the arterial sensor 6*a*, i.e. the appearance of the cross-talk pulses in the monitoring signal, based on a mathematical model of the hydraulic system in the apparatus for blood processing.

In yet another embodiment, the parameter value is calculated as an irregularity measure of the signal values in the time window of the monitoring signal. The use of an irregularity measure is based on the insight that the presence of cross-talk pulses will alter the distribution of signal values within the time window. Thus, the irregularity measure may be given by any available measure of entropy or by a statistical dispersion measure, such as standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|, \text{ or } \sum_{i=1}^{n}\sum_{j=1}^{n} |x_i - x_j|,$$

with n being the number of signal values x in the time window. Yet other examples include a measure based on a sum of absolute differences from an average value m, with the average value m being calculated for the signal values in the time window using any suitable function, such as arithmetic mean, geometric mean, median, etc. It is to be noted that all of the above suggested statistical measures also include normalized and/or weighted variants thereof.

The irregularity measures are useful with all variants of the monitoring signal, and a disruption on the venous side may be detected as a change (decrease or increase) in the irregularity measure.

In a variant, the irregularity measure is calculated as a shape measure of the histogram of the signal values in the time window. This has been found to provide a calculation-efficient and consistent detection of venous side disruption. Such an irregularity measure may be given by the so-called standardized moment of third order or higher.

The standardized moment of third order, also known as "skewness", is defined as the third central moment of a set of data samples, divided by the cube of its standard deviation:

$$y = \frac{E(x-\mu)^3}{\sigma^3},$$

where $\mu$ is the mean of x (the signal values in the time window), $\sigma$ is the standard deviation of x, and E represents the expected value. Skewness is a measure of the asymmetry of the data samples around the sample mean. If skewness is negative, the signal values are spread out more to the left of the mean than to the right. If skewness is positive, the signal values are spread out more to the right. The skewness of the normal distribution (or any perfectly symmetric distribution) is zero.

The standardized moment of fourth order, also known as "kurtosis", is defined as the fourth central moment of a set of data samples, divided by fourth power of its standard deviation:

$$k = \frac{E(x-\mu)^4}{\sigma^4}.$$

Kurtosis is a measure of how outlier-prone a distribution is. Kurtosis of a normal distribution is 3. Distributions that are more outlier-prone than the normal distribution (e.g., the Laplace distribution) have kurtosis greater than 3; distributions that are less outlier-prone have kurtosis less than 3.

It should be noted that irregularity measures may be calculated according to alternative definitions of the standardized moments. For example, one definition of kurtosis includes a subtraction of 3 such that the normal distribution yields kurtosis=0.

Figures 4C, 4D:
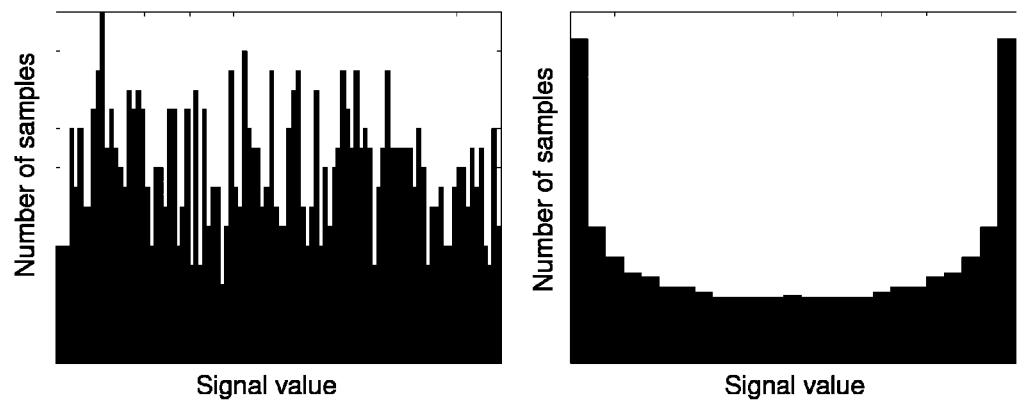

To further explain the concept of skewness and kurtosis, FIG. 4 illustrates typical histograms obtained for different distributions of signal values. FIG. 4(a) is a histogram of data samples from a normal distribution, with skewness=0 and kurtosis=3. FIG. 4(b) is a histogram of data samples from a Laplace distribution, with skewness=0 and kurtosis=6. FIG. 4(c) is a histogram of data samples from a uniform or random distribution, with skewness=0 and kurtosis=1.8. FIG. 4(d) is a histogram of data samples from a sinusoid, with skewness=0 and kurtosis=1.5. Clearly, kurtosis is indicative of the shape of the histogram.

The use of skewness and kurtosis for disruption detection will be explained in more detail for a monitoring signal of the second variant. Thus, when the blood path is intact, the monitoring signal contains both heart pulses and cross-talk pulses, where the latter act as a disturbance superimposed on the heart pulses. A venous side disruption suppresses the disturbances, while leaving the heart pulses essentially intact. Since heart pulses resemble a sinusoid, a venous side disruption is expected to produce a more sinusoidal monitoring signal compared to an intact blood path (cf. FIG. 3(a) and FIG. 3(b)). As indicated in FIG. 4, a venous side disruption may thus result in a decreased kurtosis. The venous side disruption is also likely to change the skewness of the monitoring signal, since the heart pulses typically have a skewness close to zero, or slightly negative (tilted to the left), whereas the presence of cross-talk pulses will introduce outliers in the monitoring signal, causing a change in skewness.

Figure 5:
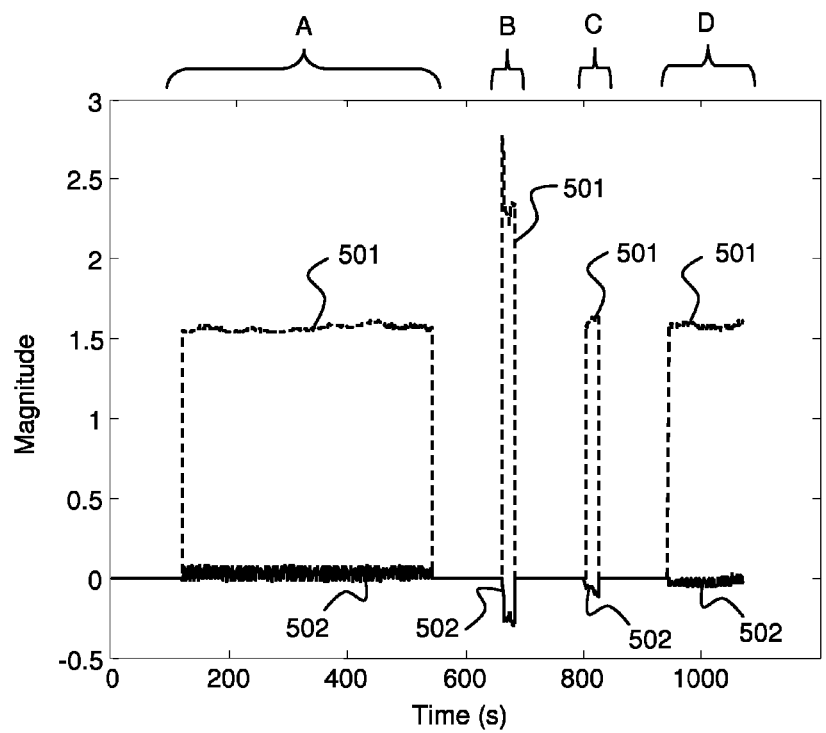
FIG. 5 is a plot of kurtosis and skewness values as a function of time for a monitoring signal obtained at different time periods before and after a VND event.

FIG. 5 is a time sequence of kurtosis values 501 and skewness values 502 calculated for a monitoring signal that contains strong heart pulses. Each kurtosis and skewness value is calculated in a 12 second sliding time window in the monitoring signal. Since the heart pulse rate typically is in the range of 1-3 Hz, the time window is selected to contain a plurality of heart pulses. The monitoring signal is acquired at different operating states during operation of a dialysis machine, as indicated by A, B, C and D in FIG. 5. In the illustrated examples, the cross-talk pulses originate primarily from the blood pump 4 (FIG. 1). In state A, the blood pump 4 is stopped at the beginning of the blood processing. In state B, the dialysis machine is operated with intact blood path to process the blood of the subject. In state C, the venous needle 2" is dislodged from the vascular access 3 (FIG. 1) during blood processing. In state D, the blood pump 4 is stopped after the dislodgement of the venous needle 2". It is clearly seen that the kurtosis values 501 decrease significantly upon the dislodgement (from state B to state C), indicating that the monitoring signal is more sinusoidal. Concurrently, the modulus (absolute value) of the skewness values 502 decreases, indicating that the monitoring signal is getting more symmetric. Thus, a venous side disruption may be detected (step S4 in FIG. 2(a)) by comparing the kurtosis or skewness values 501, 502 to a respective reference. It is also seen that the kurtosis/skewness values 501, 502 are similar in magnitude in states A, C and D. In this example, the cross-talk pulses originate entirely from the blood pump 4. In states A and D, there will be no cross-talk pulses in the monitoring signal since the blood pump 4 is stopped. Therefore, the monitoring signal in states A and D will resemble the monitoring signal in the dislodged state C. Thus, the data in FIG. 5 indicates that kurtosis/skewness values 501, 502 obtained during a blood pump stop may be used as the reference in step S4.

Figure 6:
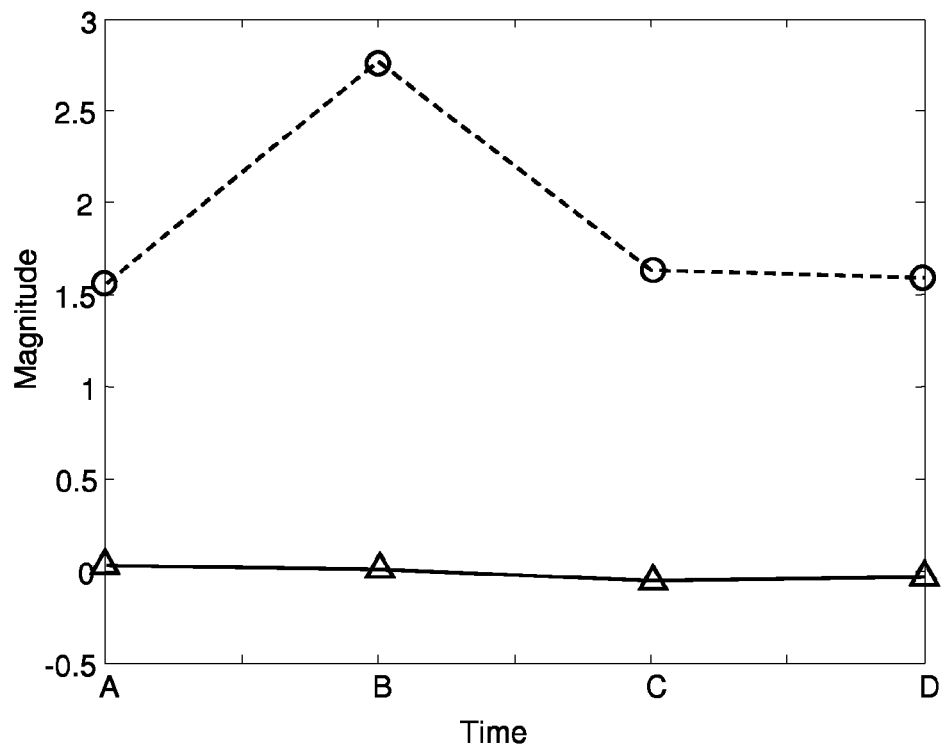
FIGS. 6-7 are plots of kurtosis and skewness values at four points in time during blood treatment on two different human subjects.

FIG. 6 is a plot of kurtosis values (O) and skewness values (Δ) calculated for the same monitoring signal as in FIG. 5, for signal values in a 20 second time window at one time point during each of the operating states A-D.

Figure 7:
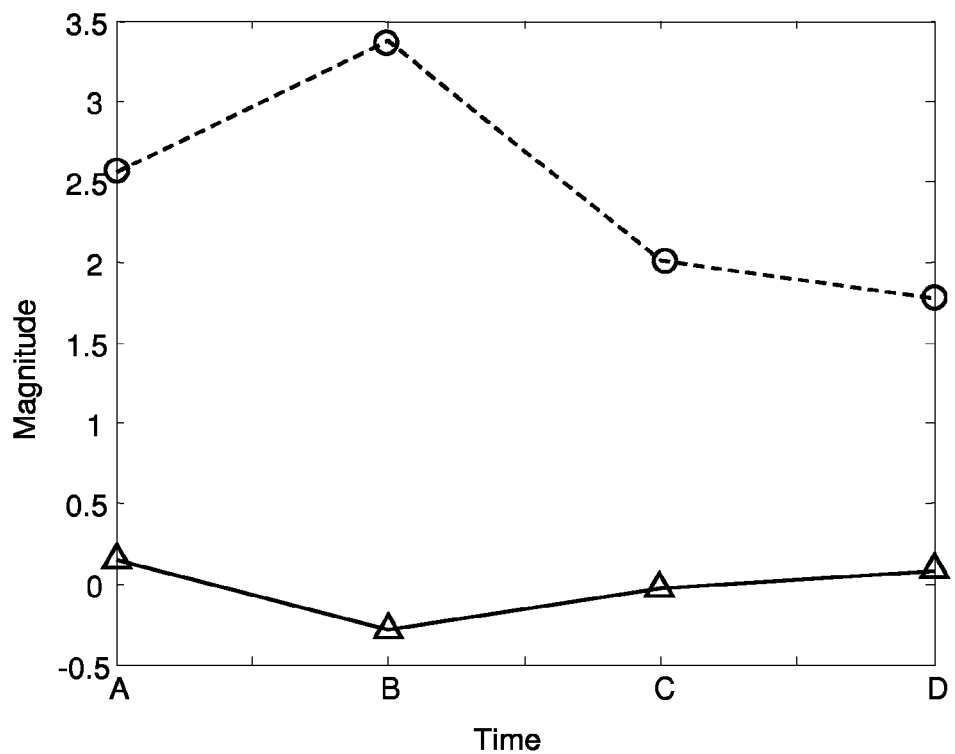

FIG. 7 is a plot of kurtosis values (O) and skewness values (Δ) calculated for a monitoring signal that contains weak heart pulses. Each kurtosis and skewness value is calculated for signal values in a 20 second time window at one time point during each of the operating states A-D. As seen, the dislodgement results in a decrease in kurtosis value and an decrease in the modulus of the skewness value.

It is to be understood that skewness and kurtosis may be useful as parameter values also if the monitoring signal is given according to the above-mentioned first, third and fourth variants. When the blood path is changed from an intact state to a disrupted stated on the venous side of the EC circuit, the distribution of the signal values in the monitoring signal is altered from one characteristic distribution to another, due to the suppression of the cross-talk pulses. However, the kurtosis/skewness values may change differently compared to FIGS. 5-7. For example, a monitoring signal of the first variant (only crosstalk pulses) is expected to yield an increased kurtosis when the venous needle is dislodged, since the presence and absence of cross-talk pulses from the blood pump 4 is expected to result in a distribution similar to FIG. 4(d) and FIG. 4(c), respectively.

It is also to be understood that the reference for use in step S4 may be obtained in other ways. If the cross-talk pulses and/or upstream pulses (also) originate from other sources than the blood pump, these sources are suitably disabled when the reference (kurtosis/skewness) is to be calculated based on the monitoring signal. The resulting reference (REF1) is representative of the heart pulses. In a variant, the reference is calculated for a monitoring signal obtained during a start-up procedure, in which the arterial side of the EC circuit 1 is connected to the vascular access 3, the venous side of the EC circuit 1 is not yet connected to the vascular access 3, and the blood pump 4 is operated to pump blood from the arterial side towards the venous side. The resulting reference (REF2) is representative of the combination of heart pulses and upstream pulses, if they are present in the monitoring signal. In a further variant, the reference is calculated for a monitoring signal obtained during a priming procedure, in which the EC circuit 1 is disconnected from the vascular access 3, and the blood pump 4 is operated to pump a priming fluid to flow into the EC circuit 1 on the arterial side and out of the EC circuit 1 on the venous side. During the priming procedure, the needles 2', 2" have typically not yet been attached to the EC circuit 1, and the priming fluid may enter the EC circuit 1 via an arterial-side connector and leave the EC circuit 1 via a venous-side connector (cf. connectors C1b and C2b in FIG. 8, below). The resulting reference (REF3) is representative of upstream pulses, if they are present in the monitoring signal.

As described above, REF1 may be used when detecting a venous side disruption based on a monitoring signal of the second variant (cross-talk pulses and heart pulses). Similarly, REF2 may be used when detecting a venous side disruption based on a monitoring signal of the third variant (cross-talk pulses, heart pulses and upstream pulses). In an alternative, a combination of REF1 and REF3, e.g. a weighted sum, may be used as an approximation of REF2 for use when detecting a venous side disruption based on a monitoring signal of the third variant. In another alternative, REF1 is used as an approximation of REF2 when detecting a venous side disruption based on a monitoring signal of the third variant, e.g. if the upstream pulses are significantly suppressed in the monitoring signal. In yet another alternative, the monitoring signal is filtered to eliminate the upstream pulses in the monitoring signal during the start-up procedure, whereby REF2 may be used when detecting a venous side disruption based on a monitoring signal of the second variant (cross-talk pulses and heart pulses). Further, REF3 may be used when detecting a venous side disruption based on a monitoring signal of the fourth variant (cross-talk pulses and heart pulses). In yet another alternative, the monitoring signal is filtered to eliminate the heart pulses in the monitoring signal during the start-up procedure (or the heart pulses are inherently absent in the monitoring signal), whereby REF2 may be used when detecting a venous side disruption based on a monitoring signal of the fourth variant. The skilled person realizes that there are further alternatives, and that generally REF1-REF3 may be regarded as different "basis values" that may be used, either alone or in combination, to form the reference for use in step S4.

The skilled person also realizes that the REF1-REF3 may be obtained to represent any other irregularity measure than kurtosis/skewness, as well as any magnitude measure. Furthermore, the above-mentioned reference profile may be obtained in a similar way as REF1-REF3, to represent only heart pulses, a combination of heart pulses and upstream pulses, or only upstream pulses. The reference profile, as well as REF1-REF3, may be retrieved from electronic memory (cf. 9 in FIG. 1), and may be generated during the current treatment session for the current subject, or in a previous treatment session for the current subject or another subject (or a plurality of subjects). As used herein, a treatment session ("session") refers to an isolated event in which a subject is first connected to the EC circuit 1, blood is extracted from and returned to the subject, and the subject is then disconnected from the EC circuit 1. The reference profile may be given, e.g., by the signal values in a time window of the monitoring signal, optionally after low-pass-filtering or time averaging.

Figure 8:
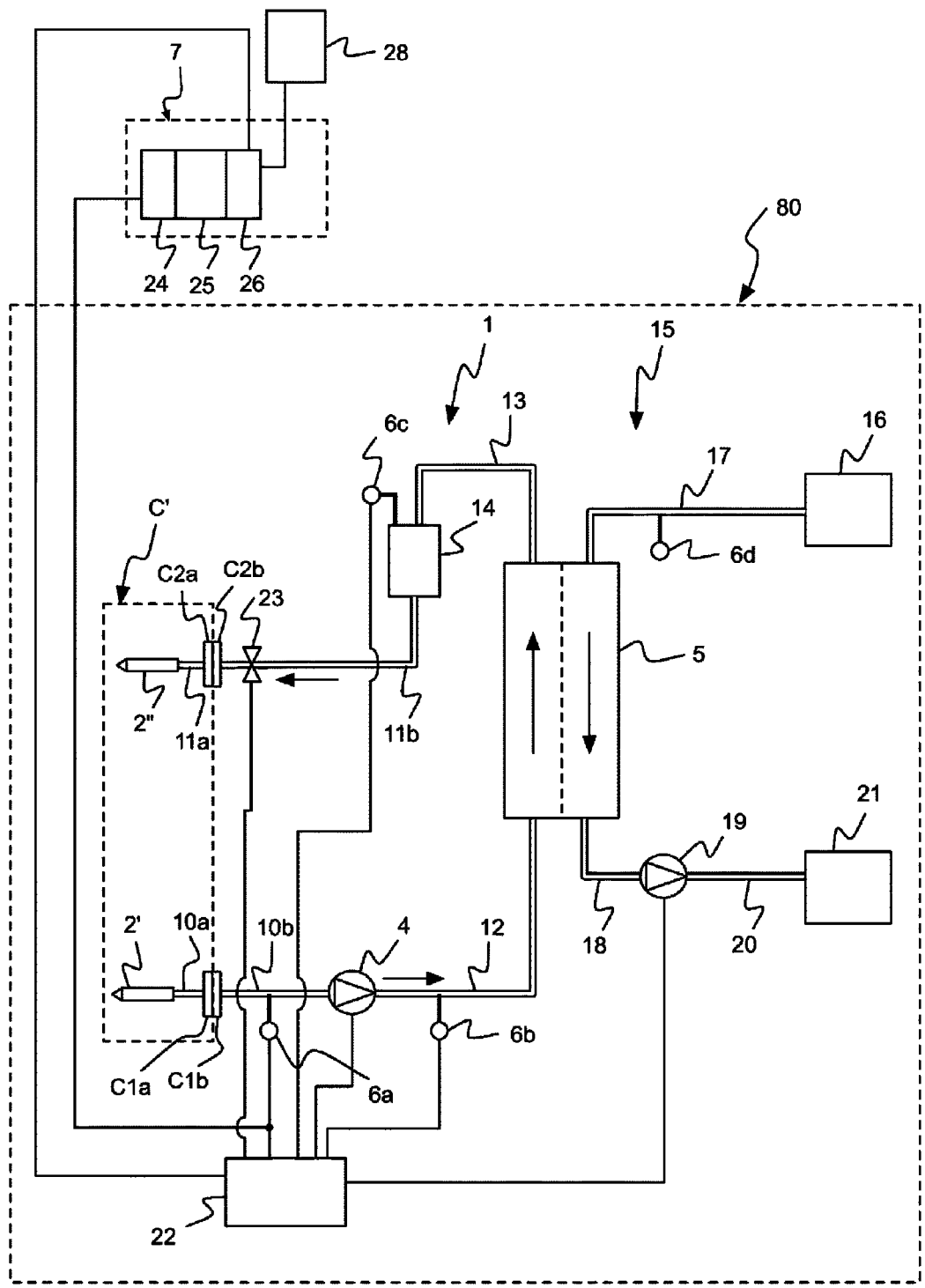
FIG. 8 is a schematic view of a system for hemodialysis treatment including an extracorporeal blood processing system and a device for VND detection.

FIG. 8 serves to further exemplify a blood processing apparatus 80, implemented as a dialysis machine, in which the inventive surveillance device 7 and the inventive method may be implemented. In FIG. 8, the dialysis machine 80 comprises an EC circuit 1 which includes a connection system C' for establishing fluid communication between the EC circuit 1 and the vascular system of a patient. The connection system C' comprises an arterial access device 2' (here in the form of an arterial needle), a connection tube segment 10a and a connector C1a. The connection system C' also comprises a venous access device 2" (here in the form of a venous needle), a connection tube segment 11a and a connector C2a. The connectors C1a, C2a are arranged to provide a releasable or permanent engagement with a corresponding connector C1b, C2b. The connectors C1a, C1b, C2a, C2b may be of any known type. In certain implementations, the connectors C1a, C1b, C2a, C2b may be omitted, whereby the connection system C' consists of the access devices 2', 2".

In FIG. 8, the EC circuit 1 further comprises an arterial tube segment 10b, and a blood pump 4 which may be of peristaltic type. On the arterial side of the blood pump 4 there is an arterial pressure sensor 6a which measures the pressure upstream of the pump 4 in the arterial tube segment 10b. The pump 4 forces the blood, via a tube segment 12, to the blood-side of the dialyser 5. The illustrated dialysis machine 80 is additionally provided with a pressure sensor 6b that measures the pressure between the blood pump 4 and the dialyser 5. The blood is led via a tube segment 13 from the blood-side of the dialyser 5 to a venous drip chamber or deaeration chamber 14 and from there back to the connection system C' via a venous tube segment 11b and the connector C2b. A pressure sensor 6c (known as "venous pressure sensor" or "venous sensor") is provided to measure the pressure on the venous side of the dialyser 5, here in the venous drip chamber 14.

In the example of FIG. 8, the venous side of the EC circuit 1 is made up of tube segment 12, the blood-side of the dialyser 5, tube segment 13, drip chamber 14, tube segment 11b, connectors C2a, C2b, tube segment 11a, and the venous access device 2", and the arterial side is made up of tube segment 10b, connectors C1a, C1b, tube segment 10a, and the arterial access device 2'.

Both the arterial needle 2' and the venous needle 2" are connected to a vascular access (cf. 3 in FIG. 1). Depending on the type of vascular access, other types of access devices may be used instead of needles, e.g. catheters. The vascular access 3 may be of any suitable type, including different types of venovenous (VV) blood accesses and different types of arteriovenous (AV) access, such as a graft or a fistula.

The dialysis machine 80 also comprises a dialysis fluid circuit 15, here exemplified as a source 16 of dialysis fluid, a tube segment 17, a dialysis fluid-side of the dialyser 5, a tube segment 18, a dialysis fluid pump 19, a tube segment 20, and an outlet/drain 21. It is to be understood that FIG. 8 is schematic and exemplary, and that the dialysis fluid circuit 15 may include other components, such as further pumps, further flow paths, flow-controlling valves, chambers, etc. A pressure sensor 6d is provided to measure the fluid pressure in the dialysis fluid circuit 15.

The dialysis machine 80 further comprises a central control unit 22 that controls the operation of the dialysis machine 80. In FIG. 8, the control unit 22 is connected to operate the pumps 4, 19, and to acquire data from the pressure sensors 6a-6c. If a fault condition is detected, the control unit 22 may activate an alarm and/or stop the blood flow, e.g. by stopping the blood pump 4 and activating one or more clamping devices 23 (only one shown) on the tube segments 10b, 11b, 12, 13. Although not shown or discussed further it is to be understood that the control unit 22 may control many other functions, e.g. the temperature and composition of the dialysis fluid, additional pumps, etc.

The surveillance device 7 is connected to the arterial pressure sensor 6a and is operable to identify any disruption that causes the cross-talk pulses to disappear, or at least decrease significantly in magnitude, in the monitoring signal. Such disruption may be caused by a dislodgement of the venous access device 2" from the vascular access 3, commonly known as VND (Venous Needle Dislodgement), a separation of the connectors C2a, C2b, a break or kinking of any of the tube segments 11a, 11b, 12, 13, a break or clogging in the dialyzer 5, a leakage of the venous drip chamber 14, or a separation of any tube segment connections, e.g., the connection between any of the tube segments 12, 13 and the dialyzer 5. A corresponding disruption may occur on the arterial side, and may e.g. be detected via the presence/absence of heart pulses in the monitoring signal.

In FIG. 8, the device 7 comprises a data acquisition part 24 for sampling or otherwise acquiring the pressure data from the arterial sensor 6a and for processing the pressure data so as to generate the above-mentioned monitoring signal. Thus, the data acquisition part 24 implements steps S1 and S2 in FIG. 2(a). For example, the data acquisition part 24 may include an A/D converter with a required minimum sampling rate and resolution and one or more signal amplifiers. The data acquisition part 24 may also comprise one or more analog or digital filters operable to remove undesired signal components in the pressure data. The resulting monitoring signal is provided as input to a data analysis part 25 which executes the actual surveillance process, represented by steps S3 and S4 in FIG. 2(a). The device 7 further comprises an output interface 26 for outputting data, e.g. a control signal causing the control device 22 to stop the blood pump 4 and/or activate the clamping device(s) 23. The output interface 26 may also be tethered or wirelessly connected to a local or remote device 28 for generating an audible/visual/tactile alarm or other warning signal. The device 7 may be implemented as a separate unit connected to the dialysis machine 80 (as shown), or it may be incorporated as part of the dialysis machine 80, e.g. as part of the control device 22.

An alternative representation of the surveillance device 7 is shown in FIG. 2(b). Here, the surveillance device 7 includes an element (or means) 201 for obtaining the pressure signal from the arterial sensor 6a, and an element (or means) 202 for processing the pressure signal for generation of the monitoring signal to contain the cross-talk pulses. There is also provided an element (or means) 203 for calculating of the parameter value that indicates a presence or absence of the cross-talk pulses, and an element (or means) 204 for evaluating the parameter value for detection of a venous side disruption. The device 7 also comprises an element (or means) 205 for outputting data on the outcome of the evaluation.

Irrespective of representation, the surveillance device 7 may be implemented by special-purpose software (or firmware) run on one or more general-purpose or special-purpose computing devices. In this context, it is to be understood that an "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases.

Such a software controlled computing device may include one or more processing units (cf. 8 in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The surveillance device 7 may further include a system memory and a system bus that couples various system components including the system memory (cf. 9 in FIG. 1) to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The surveillance device 7 may include one or more communication interfaces, such as a serial interface, a parallel interface, a USB interface, a wireless interface, a network adapter, etc, as well as one or more data acquisition devices, such as an A/D converter. The special-purpose software may be provided to the surveillance device on any suitable computer-readable medium, including a record medium, a read-only memory, or an electrical carrier signal.

It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art.

While the invention has been described in connection with what is presently considered to be the most practical and preferred embodiments, it is to be understood that the invention is not limited to the disclosed embodiments, but on the contrary, is intended to cover various modifications and equivalent arrangements included within the spirit and the scope of the appended claims.

For example, the pressure sensor may be of any type, e.g. operating by resistive, capacitive, inductive, magnetic, acoustic or optical sensing, and using one or more diaphragms, bellows, Bourdon tubes, piezo-electrical components, semiconductor components, strain gauges, resonant wires, accelerometers, etc. For example, the pressure sensor may be implemented as a conventional pressure sensor, a bioimpedance sensor, a photoplethysmography (PPG) sensor, etc.

Likewise, the blood pump may be of any type, not only a rotary peristaltic pump as indicated above, but also any other type of positive displacement pump, such as a linear peristaltic pump, a diaphragm pump, or a centrifugal pump.

Furthermore, it is conceivable to use a combination of parameter values to detect the venous side disruption, including different parameters of the same type (e.g. magnitude, matching and irregularity), as well as parameters of the same type.

It is also to be understood that the inventive technique may be used in combination with conventional techniques, e.g. as described in the Background section.

It is also to be understood that the above-described irregularity measure, and in particular the standardized moment of third order or higher, may be used to provide a calculation-efficient implementation of the disruption detection technique suggested by WO97/10013, namely detecting presence/absence of pump pulses at the venous pressure sensor, which pump pulses may originate from the blood pump (and/or other pulse generators on the arterial side) and have propagated in a direction upstream from the blood pump via the arterial needle, the vascular access and the venous needle to the venous pressure sensor.

The invention claimed is:

1. A monitoring device for monitoring a blood path extending from a blood vessel access of a human subject through an extracorporeal blood processing apparatus and back to the blood vessel access, wherein the blood path comprises a blood withdrawal device and a blood return device for connection to the blood vessel access, and a pumping device operable to pump blood through the blood path from the blood withdrawal device to the blood return device, said monitoring device comprising:
- an input for obtaining pressure data from a pressure sensor arranged upstream of the pumping device in the blood path to detect pressure pulses in the blood pumped through the blood path; and
- a signal processor connected to said input and being configured to:
- generate, based on the pressure data, a time-dependent monitoring signal comprising cross-talk pulses that originate from one or more pulse generators in the extracorporeal blood processing apparatus and have propagated in a direction downstream of the pumping device through the blood return device, the blood vessel access and the blood withdrawal device to the pressure sensor,
- process the monitoring signal for calculation of a parameter value that indicates a presence or absence of the cross-talk pulses, and
- detect, based at least partly on the parameter value, a disruption of the blood path downstream of the pumping device.

2. The monitoring device of claim 1, wherein the signal processor is configured to calculate the parameter value as a measure of irregularity of signal values within a time window of the monitoring signal.

3. The monitoring device of claim 2, wherein the measure of irregularity includes a measure of entropy of the signal values.

4. The monitoring device of claim 2, wherein the measure of irregularity includes a statistical measure of the signal values.

5. The monitoring device of claim 4, wherein the statistical measure includes a standardized moment of third order or higher.

6. The monitoring device of claim 4, wherein the statistical measure includes at least one of skewness and kurtosis.

7. The monitoring device of claim 2, wherein the signal processor is configured to generate the monitoring signal to comprise physiological pulses that originate from one or more physiological pulse generators in the human subject, and wherein the time window is selected so as to include at least part of one physiological pulse.

8. The monitoring device of claim 7, wherein the parameter value is calculated to represent a disturbance caused by the superposition of the cross-talk pulses on the physiological pulses.

9. The monitoring device of claim 7, wherein the signal processor is configured to generate the monitoring signal by filtering the pressure data to at least suppress interference pulses that originate from the pumping device and have propagated in the blood path in a direction upstream of the pumping device, wherein the filtering is configured to suppress the interference pulses such that the ratio in magnitude between the interference pulses and the physiological pulses in the monitoring signal is less than about $1/10$.

10. The monitoring device of claim 1, wherein the signal processor is configured to generate the monitoring signal by filtering the pressure data with respect to interference pulses that originate from the pumping device and have propagated in the blood path in a direction upstream of the pumping device, wherein the filtering is configured to suppress the interference pulses compared to the cross-talk pulses.

11. The monitoring device of claim 10, wherein the signal processor is configured to essentially remove the interference pulses when filtering the pressure data to generate the monitoring signal.

12. The monitoring device of claim 1, wherein the signal processor is configured to generate the parameter value as a measure of magnitude of the signal values within a time window of the monitoring signal.

13. The monitoring device of any preceding claim 1, wherein the signal processor is configured to detect the disruption by comparing the parameter value to a reference, which is obtained as an estimate of the parameter value in absence of the cross-talk pulses.

14. The monitoring device of claim 13, wherein the signal processor is configured to obtain the reference based on at least one of a first, second and third basis value, wherein the first basis value is given by the parameter value calculated during a time period in which said at least one pulse generator is disabled, the second basis value is given by the parameter value calculated during a start-up procedure, in which the extracorporeal blood processing apparatus is connected to the blood vessel access via the blood withdrawal device but is disconnected from the blood vessel access downstream of the pumping device, and the pumping device is operated to pump blood from the blood withdrawal device into the extracorporeal blood processing apparatus, and the third basis value is given by the parameter value calculated during a priming procedure, in which the extracorporeal blood processing apparatus is disconnected from the blood vessel access upstream and downstream of the pumping device, and the pumping device is operated to pump a priming fluid to flow into the extracorporeal blood processing apparatus at an upstream end and out of the extracorporeal blood processing apparatus at a downstream end.

15. The monitoring device of claim 14, wherein the first basis value is generated to represent presence of physiological pulses that originate from the human subject and absence of said cross-talk pulses and absence of interference pulses that originate from the pumping device and have propagated in the blood path in a direction upstream of the pumping device; wherein the second basis value is generated to represent one of: presence of said physiological pulses and said interference pulses and absence of said cross-talk pulses; presence of said physiological pulses and absence of said cross-talk pulses and said interference pulses; and presence of said interference pulses and absence of said cross-talk pulses and said physiological pulses; and wherein the third basis value is generated to represent presence of said interference pulses and absence of said cross-talk pulses and said physiological pulses.

16. The monitoring device of claim 1, wherein the signal processor is configured to extract shape-indicative data from the monitoring signal and calculate the parameter value by matching the shape-indicative data to reference profile data.

17. The monitoring device of claim 16, wherein the shape-indicative data comprises signal values in the monitoring signal, and the reference profile data comprises a temporal reference profile.

18. The monitoring device of claim 1, wherein said one or more pulse generators are included in a dialysis fluid circuit in hydraulic contact with the blood path, and wherein the signal processor is configured to obtain a reference signal from a further pressure sensor arranged in the dialysis fluid circuit to detect pressure pulses in a dialysis fluid pumped through the dialysis fluid circuit or from a control signal for said one or more pulse generators, and calculate the parameter value by matching the monitoring signal to the reference signal.

19. A device for monitoring a blood path extending from a blood vessel access of a human subject through an extracorporeal blood processing apparatus and back to the blood vessel access, wherein the blood path comprises a blood withdrawal device and a blood return device for connection to the blood vessel access, and a pumping device operable to pump blood through the blood path from the blood withdrawal device to the blood return device, said device comprising a processor executing instructions stored on a non-transitory memory to cause the device to:
    obtain pressure data from a pressure sensor arranged upstream of the pumping device in the blood path to detect pressure pulses in the blood pumped through the blood path;
    generate, based on the pressure data, a time-dependent monitoring signal comprising cross-talk pulses that originate from one or more pulse generators in the extracorporeal blood processing apparatus and have propagated in a direction downstream of the pumping device through the blood return device, the blood vessel access and the blood withdrawal device to the pressure sensor;
    calculating, using the monitoring signal, a parameter value that indicates a presence or absence of the cross-talk pulses; and
    detecting, based at least partly on the parameter value, a disruption of the blood path downstream of the pumping device.

20. An apparatus for extracorporeal blood processing, which is configured for connection to the cardiovascular system of a human subject so as to define a blood path extending from a blood vessel access of the human subject and comprising a blood withdrawal device for connection to the blood vessel access, a pumping device operable to pump blood through the blood path, a blood processing unit, and a blood return device for connection to the blood vessel access, said apparatus further comprising the monitoring device as set forth in claim 1.

21. A method of monitoring a blood path extending from a blood vessel access of a human subject through an extracorporeal blood processing apparatus and back to the blood vessel access, wherein the blood path comprises a blood withdrawal device and a blood return device for connection to the blood vessel access, and a pumping device operable to pump blood through the blood path from the blood withdrawal device to the blood return device, said method comprising:
    obtaining pressure data from a pressure sensor arranged upstream of the pumping device in the blood path to detect pressure pulses in the blood pumped through the blood path;
    generating, based on the pressure data, a time-dependent monitoring signal comprising cross-talk pulses that originate from one or more pulse generators in the extracorporeal blood processing apparatus and have propagated in a direction downstream of the pumping device through the blood return device, the blood vessel access and the blood withdrawal device to the pressure sensor;
    processing the monitoring signal for calculation of a parameter value that indicates a presence or absence of the cross-talk pulses; and
    detecting, based at least partly on the parameter value, a disruption of the blood path downstream of the pumping device.

22. A non-transitory computer-readable medium storing instruction for execution by a processor for an extracorporeal blood processing apparatus including a blood pump configured to pump blood through an extracorporeal blood passage and a pressure sensor monitoring a pressure in the extracorporeal blood passage, wherein the extracorporeal blood passage extends from a blood vessel access of a human subject through an extracorporeal blood processing apparatus and back to the blood vessel access, wherein the processor executes the instructions to cause the:
    obtain pressure data from the pressure sensor arranged upstream of the blood pump in the blood passage, wherein the pressure data indicates pressure pulses in the blood flowing through the blood passage;
    generate, based on the pressure data, a time-dependent monitoring signal which includes cross-talk pulses, wherein the cross-talk pulses originate from at least one pulse generator in the extracorporeal blood processing apparatus and have propagated through the blood flowing downstream of the pump in the blood passage;
    calculating, using the monitoring signal, a parameter value that indicates a presence or absence of the cross-talk pulses; and
    detecting, based at least partly on the parameter value, a disruption of the blood path downstream of the pumping device.

* * * * *